(12) United States Patent
Tait et al.

(10) Patent No.: US 6,598,994 B1
(45) Date of Patent: *Jul. 29, 2003

(54) MULTI-ANGLE INSPECTION OF MANUFACTURED PRODUCTS

(75) Inventors: Robert W. Tait, Brighton, MI (US);
Alvaro D. Lewin, Austin, TX (US);
Mark R. DeYong, Round Rock, TX (US)

(73) Assignee: Intelligent Reasoning Systems, Inc., Round Rock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/620,172

(22) Filed: Jul. 19, 2000

Related U.S. Application Data (63) Continuation-in-part of application No. 09/139,172, filed on Aug. 24, 1998, now Pat. No. 6,161,941.

(51) Int. Cl.[7] .............................................. F21V 21/00
(52) U.S. Cl. ...................... 362/249; 362/231; 362/283; 362/347; 362/350; 362/800
(58) Field of Search .............................. 362/249, 282, 362/252, 283, 860, 347, 350, 235, 231

(56) References Cited

U.S. PATENT DOCUMENTS

| | | | |
|---|---|---|---|
| 5,038,258 A | 8/1991 | Koch et al. | 362/237 |
| 5,039,868 A | 8/1991 | Kobayashi et al. | 250/572 |
| 5,309,277 A | 5/1994 | Deck | 359/387 |
| 5,920,643 A | 7/1999 | White et al. | 382/141 |
| 5,982,493 A | 11/1999 | Lehman et al. | 356/375 |
| 6,017,133 A | 1/2000 | Grasmuller et al. | 362/252 |
| 6,022,124 A | 2/2000 | Borun et al. | 362/247 |
| 6,033,087 A * | 3/2000 | Shozo et al. | 362/19 |
| 6,141,033 A * | 10/2000 | Michael et al. | 348/25 |
| 6,286,978 B1 * | 9/2001 | Tait et al. | 362/249 |

FOREIGN PATENT DOCUMENTS

| | | | | |
|---|---|---|---|---|
| WO | 9944409 A | 2/1999 | | H05K/13/08 |
| WO | 00/11400 | 1/2000 | | F21V/21/00 |

* cited by examiner

*Primary Examiner*—Sandra O'Shea
*Assistant Examiner*—John Anthony Ward
(74) *Attorney, Agent, or Firm*—Gray Cary Ware & Freidenrich, LLP (57) ABSTRACT

An illumination system for inspection of devices is disclosed. The system includes a frame for positioning over an image area. A plurality of light source groups are coupled with the frame and are each configured to produce one or more wavelengths of light. Each light source group is configured to produce a wavelength of light which is not produced by another light source group.

51 Claims, 7 Drawing Sheets

MULTI-ANGLE INSPECTION OF MANUFACTURED PRODUCTS

RELATED APPLICATIONS

This application is a continuation-in-part of the U.S. patent application granted Ser. No. 09/139,172, filed Aug. 24 1998 now U.S. Pat. No. 6,161,941, and entitled LIGHT ARRAY SYSTEM AND METHOD FOR ILLUMINATION OF OBJECTS IMAGED BY IMAGING SYSTEMS which is incorporated herein in its entirety.

BACKGROUND

1. Field of the Invention

The invention relates generally to illumination systems, and more particularly to a light array system for illumination of objects to be inspected.

2. Background of the Invention

Inspection of manufactured products helps to reduce the number of defective products introduced into the marketplace. The effectiveness of certain types of inspections, for example inspections of printed circuit boards or printed wiring boards (collectively "PWBs"), is often dependent upon the illumination systems and processes used to provide inspection lighting of the manufactured product during inspection.

This is especially true for automated inspection of PWBs using line scan cameras—the ability to identify, classify, and properly detect defects in the inspected PWBs is greatly affected by the lighting available on the subject PWB. Proper illumination allows for enhanced visibility of PWB manufacturing defects, including raw paste analysis (coverage and volume, missing/mis-aligned/damaged components, bent/missing/lifted leads, bridges and near bridges, alignment gauging, insufficient and excess solder, solder dewets, cold and fractured solder joints, etc.).

Several different illumination methodologies have been used for PWB inspection as well as other inspection tasks. These illumination techniques include highly diffuse ("cloudy day") illumination, direct illumination, re-directed illumination using fiber optics to distribute the source over a line, projected images of lines, ring lights, coaxial illumination, flood lights, as well as all of the above with some form of additional diffuser. Each of these methods proves inadequate when used for automated inspection of PWBs using a line scan camera for at least one or more of the following reasons: (1) inadequate overall light level; (2) excessive localized blooming or glinting (i.e., saturation of camera imaging elements due to excessive light); (3) insufficient coverage of light to fill shadows; and (4) image shiny, near vertical objects, such as leads.

For example, fixed angle single light sources cannot provide lighting to shadowed areas (such as shorter components surrounded by taller components or areas under vertical leads perpendicular to the scan direction). In order to get the light intensity required for inspection, these fixed angle light sources can also cause "blooming" or very bright spots in the camera (due to the angle of reflection) that prevent inspection of that area because nothing could be discerned from the blooming area. In addition, because solder fillets are "mound-shaped", regardless of the light angle variation, some reflection in a specular fashion back to the camera will occur. To a line scan camera, the shadow areas often look lack while the shiny or blooming areas look white and accurate detection of efects in these areas is difficult or impossible.

For the above reasons, there is a need for improving the automated inspection of devices such as PWBs.

SUMMARY OF THE INVENTION

The present invention provides an illumination system that substantially eliminates or reduces disadvantages and problems associated with previously developed illumination systems and methods used for automated inspection.

One embodiment of the invention relates to an illumination system for inspection of devices. The system includes a frame for positioning over an image area. A plurality of light source groups are coupled with the frame and are each configured to produce one or more wavelengths of light. Each light source group is configured to produce a wavelength of light which is not produced by another light source group.

In one embodiment of the illumination system, the light source groups are arranged such that each light source group includes the light sources producing a light beam with a central ray which is incident on the image area within a particular range of incident angles.

One embodiment of the system includes a plurality of light source groups coupled with the frame and configured to produce one or more wavelengths of light. Electronics control the wavelength of light produced by the light source groups such that each light source group produces a wavelength of light which is not produced by another light source group.

Another embodiment of the invention relates to a method for inspecting a device. The method includes positioning a frame over an image area. The frame includes a plurality of light source groups which are each configured to produce one or more wavelengths of light. Each light source is group configured to produce a wavelength of light which is not produced by another light source group. The method also includes generating a plurality of images. Each image is generated from the light produced by a different light source group.

Yet another embodiment of the invention relates to a method of illuminating a device to be inspected. The method includes positioning a frame over an image area and illuminating the image area from a plurality of light source groups attached to the frame. Each light source group is configured to produce a wavelength of light which is not produced by another light source group.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

The present invention provides an illumination system that illuminates an image area simultaneously from a wide variety of angles while at the same time maintaining a high enough light intensity for the inspection camera to take a quality image. The geometry of a dome light array having dual side panel light arrays combined with high power LED light sources provides the variety of illumination angles and required light intensity to improve the image quality, reliability and speed of camera-based inspections. The illumination system of the present invention is particularly well suited for illumination of single dimensional devices automatically inspected using a line scan camera.

Imaging devices configured to generate images using particular wavelengths of light can be used to concurrently generate multiple images of the device. For instance, imaging devices such as line scan cameras often include a channel configured to generate an image using red light, a channel configured to generate an image using green light and another channel configured to generate an image using blue light. Such an illumination system can include a first light source group configured to produce red light, a second light source group configured to produce green light and a third light source group configured to produce blue light. Hence, a channel of the line scan camera can generate a first image from the light produced by the first light source group, another channel can generate a second image from the light produced by the second light source group and another channel can generate a third image from the light produced by the third light source group. Images generated using different wavelengths of light can reveal different features of a device.

In one embodiment of the illumination system, the light source groups are arranged such that each light source group includes the light sources producing a light beam with a central ray which is incident on the image area within a particular range of incident angles. Accordingly, each of the images can be generated using light which illuminates the device at a different range of incident angles.

Having images of an object or a device which are associated with different incident angles can enhance the inspection process. For instance, when examining devices on a PWB, low incident angle illumination may enhance edges to a greater extent than high incident angle illumination, however, higher incident angle illumination is more useful for inspection of plated through holes than is lower incident angle illumination. As a result, the image associated with low incident angle illumination is consulted for edge inspection while the image associated with higher angle illumination is consulted for plated through hole inspection.

Figure 1:
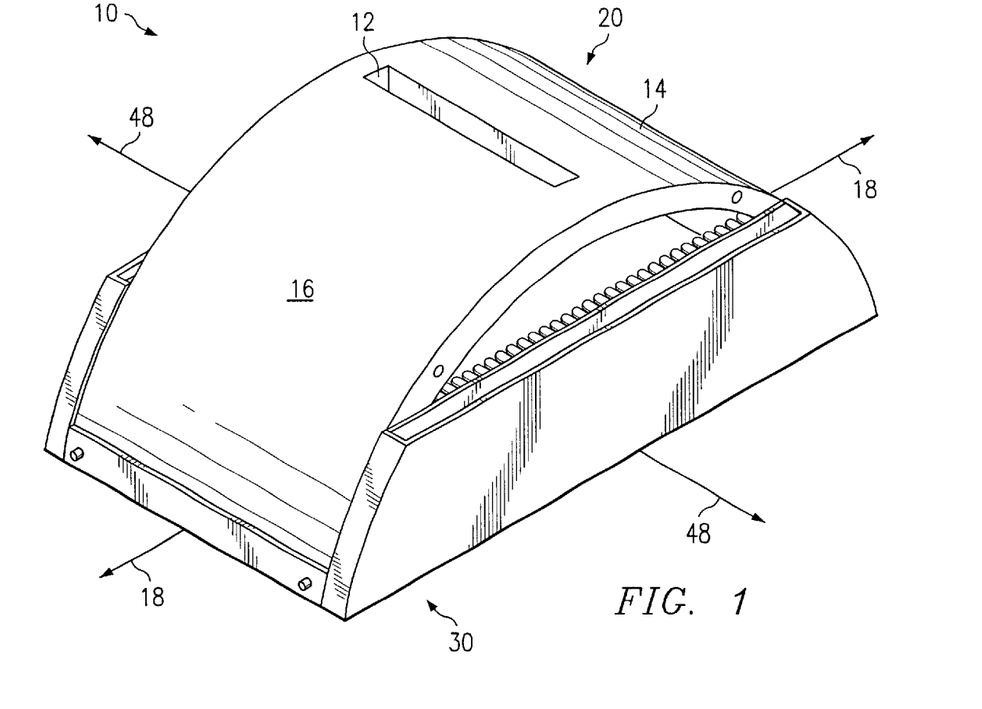
FIG. 1 shows a top perspective view of one embodiment of the illumination system of the present invention.
Figure 2:
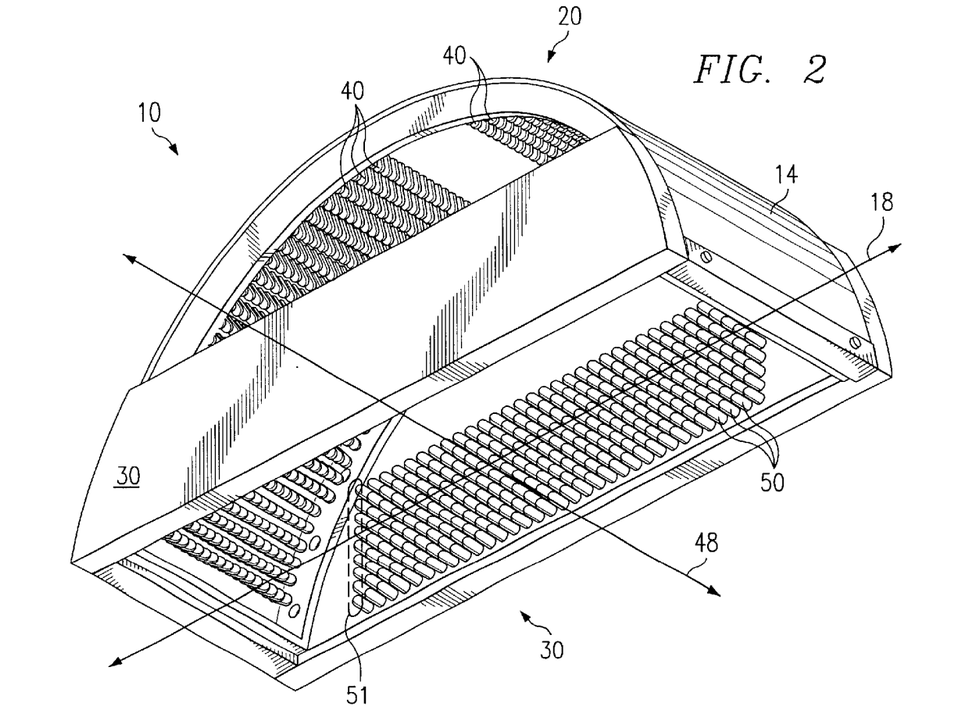
FIG. 2 shows a bottom perspective view of the embodiment of FIG. 1.

FIG. 1 shows a top perspective view of one embodiment of the illumination system 10 of the present invention. The illumination system 10 includes a frame 14. A suitable shape for the dome includes, but is not limited to, a cylindrical dome and a semi-cylindrical dome. The frame supports a dome light array 20 and one or more side panel light arrays 30 coupled to both sides of the dome light array 20. The side panel light array 30 can be integral with the dome light array 20 or can be detachable from the dome light array 20. As shown in FIG. 2 a plurality of light sources 40 can be attached to the dome light array 20. The dome light array 20 also includes an aperture 12 through which an imaging device, such as a line scan camera, can take images of a device such as a PWB to be inspected. Scan axis 18 illustrates the axis that coincides with the scan direction for the embodiment of the illumination system of FIG. 1. Image axis 48 is perpendicular to the scan axis 18 along the image plane 22. The frame 14 can be formed in a variety geometries but is preferably formed in the shape of a partial circle, as viewed from either side, where the radius of the circle originates at the image axis. The dome light array 20 thus forms a partial cylinder along and about image axis 48. The width of the aperture 12 and the imaging device constraints define the imaging width of the image taken. While the present invention will be described herein for the specific application of inspection of devices such as PWBs using an imaging device, it should be understood that the application of the present invention extends beyond that specific application.

FIG. 2 is a bottom perspective view of the FIG. 1 embodiment that shows the plurality of light sources 40 of dome light array 20. Light sources 40 can include light emitting diodes (LEDs), optic lights, and other lighting elements that provide adequate light intensity. As shown, the plurality of light sources 40 can be arranged in rows where each row is an arc along radius R. In the embodiment of FIG. 2, side panel light arrays 30 having a plurality of light sources 40 are attached to each side of dome light array 20 normal to image axis 48. The FIG. 2 embodiment also shows light sources 40 aligned in parallel vertical rows 51. It should be understood that this configuration with approximately parallel rows is optional and other configurations of light sources 40 on side panel light array 30 can be used in conjunction with the present invention.

Figure 3:
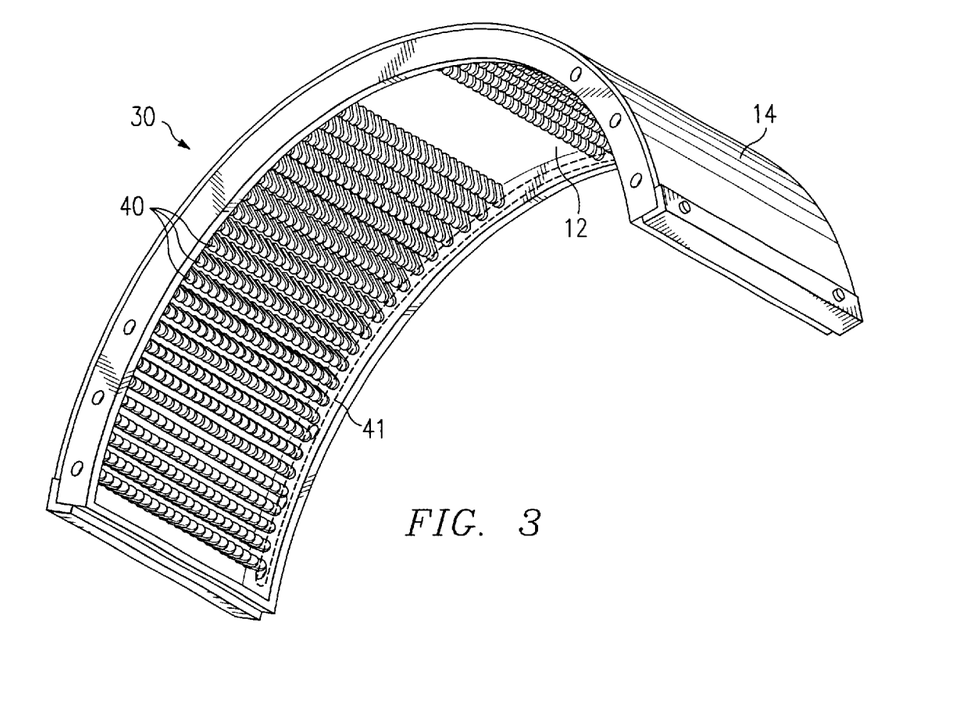
FIG. 3 shows a front end view of an embodiment of the dome light array of the present invention including light sources that are light emitting diodes or LEDs.

FIG. 3 shows a front view of frame 14 with light sources 40 attached and aperture 12 cut out from the top of frame 14. As shown in the embodiment of FIGS. 2 and 3, the dome light array 20 is a portion of a cylinder about image axis 48, having a radius R where the light sources 40 are positioned so that each light source 40 points approximately to the image axis 48 (i.e., the center point of the cylinder that coincides with the originating point of radius R) which is coincident with (or contained within) the imaging area. The imaging area is the area of the imaging plane that will be imaged by the line scan camera through aperture 12. The imaging area and imaging plane will be described in further detail. The FIG. 3 embodiment shows rows 41 of light sources 40 around the cylinder of dome light array 20. The rows 41 are approximately parallel with each row 41 being one light source in depth. It should be understood that the spacing within and between rows of light sources, or even whether there are "rows" per say is optional to the specific application.

Pointing each light source 40 at approximately the originating point of the radius (i.e., the center of the circle as viewed from the side or the cylinder of the dome light array 40) assures that each light source 40 contributes to the overall lighting scheme. If each light source 40 has the same intensity, then each light source 40 would then contribute equally to the illumination of the imaging area.

During inspection, a device will be placed underneath the dome light array 20 so that the light from the multiple light sources 40 will illuminate an imaging area (this imaging area will be coincident with the radius R originating point). Furthermore, the light from the light sources 40 in side panel light arrays 30 will also provide additional illumination on and/or around the imaging area. An imaging device will generate an image of the device on the imaging area through aperture 12. Either the device or imaging device will then be moved relative to one another so that a different area on the device is now within the imaging area and another picture will be taken. This is repeated until the areas of interest on the device have all been photographed for inspection.

Figure 5:
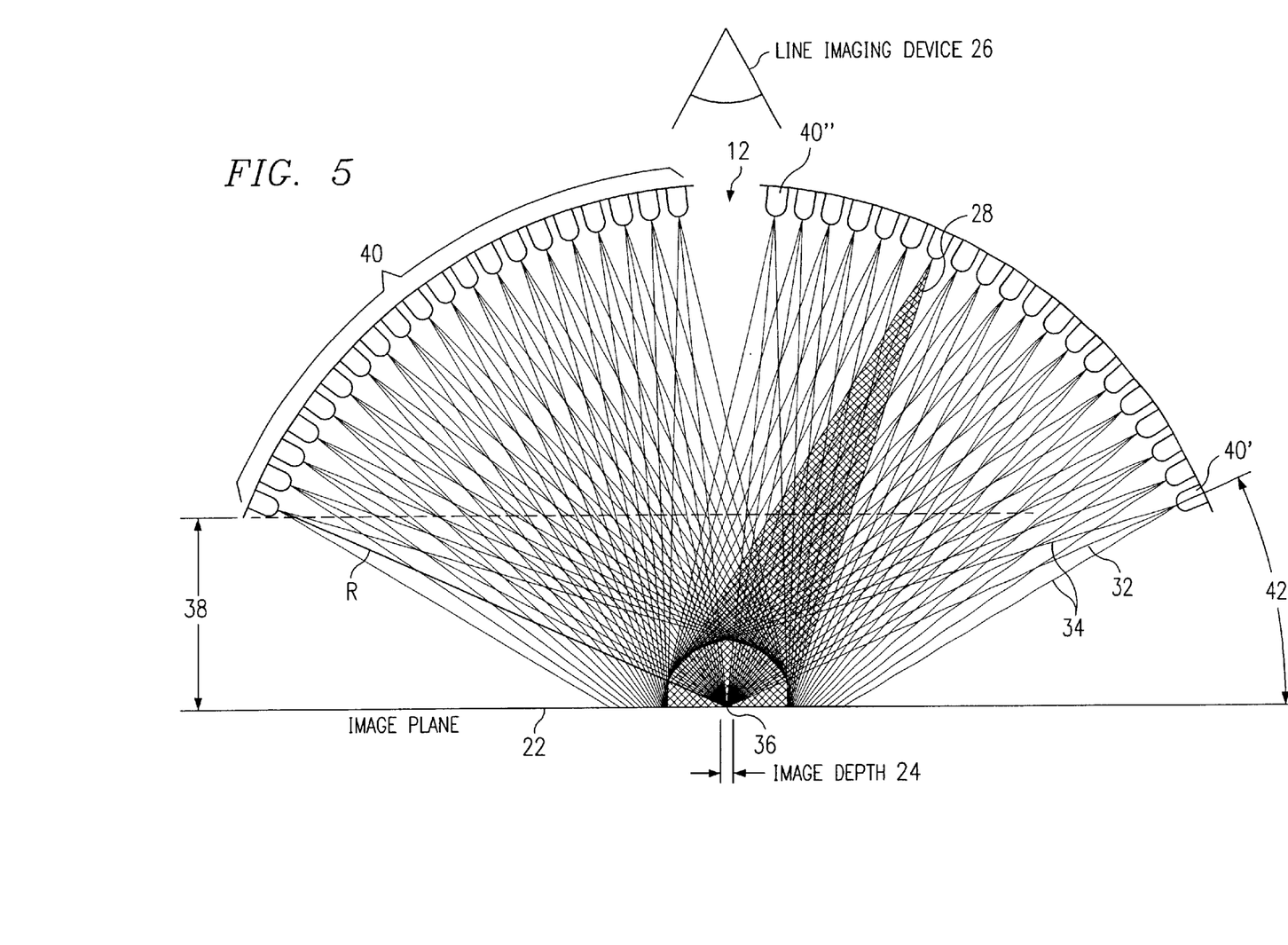
FIG. 5 is a one dimensional representation of the light produced by each light source LED in one row of LEDs of the dome light array and illustrates the cumulative light effect at the image area.

FIG. 5 is a one-dimensional, side view representation of one section of the dome light array 20 as viewed along the image axis that shows a profile of the cumulative light effect of the light sources 40 on the image area 60. The imaging device 26 takes an image of a device on the image area 60, where the image has an image depth 24 as defined by the imaging device 26 and the particular application. As shown in FIG. 5, each light sources 40 is shown with a central ray 32 and outer rays 34 that define the light source's angle of illumination. This angle of illumination defined by the cone of outer rays 34 can vary depending on the type and number of light sources 40 used (i.e., depending on the spacing between light sources 40). As can be seen, the distance between each light source 40 and image point 36 along central ray 32 is defined by radius R. Each light source 40 directly illuminates the image area 60. The clearance 38 shows the distance from the bottom of the dome light array 20 to the image plane 22. Clearance distance 38 should preferably be minimized and is a function of the height of components rising from the imaged object above the image plane. For example, in an automated PWB inspection system using a line scan camera, the PWB board will typically define the image plane 22 while the components will rise above the image plane 22 to certain heights. As the device is moved from position to position in order to image all required areas on the device, the clearance distance 38 must be sufficient to allow the device or the imaging device to be moved on the image plane 22 without causing interference between the illumination system 10 and the components on the device. Incident angle 42 represents the lowest angle of illumination available and is a function of the radius R and the clearance distance 38.

Figure 6:
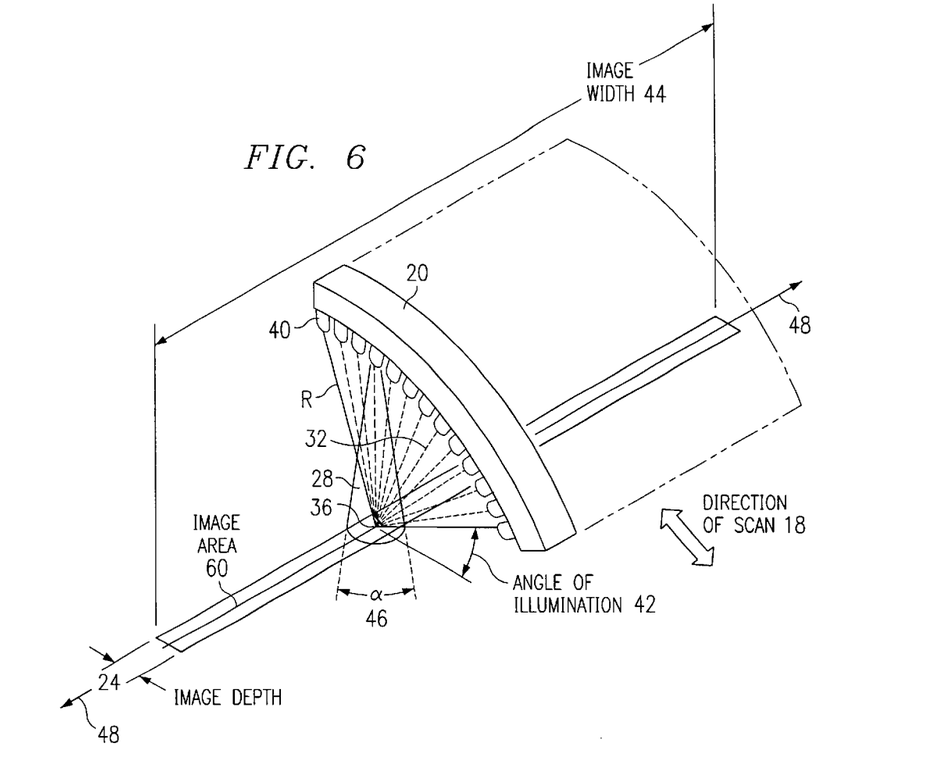
FIG. 6 shows a partial section of a one light source-depth row of the dome light array of FIG. 2.

FIG. 6 further illustrates the illumination from wide angles from the dome light array 20 on the image area 60. The dome light array section shown in FIG. 6 shows one row of arcs of light sources 40. Each row of light sources 40 along the arc defined by radius R provides illumination 28 onto image area 60 (defined as the image width 44 by the image depth 24) having illumination area 46. The device or the imaging device moves along the direction of scan along the scan axis 18. Each light source 40 is positioned at an angle of illumination 42 such that its central ray 32 is approximately pointed at the image point 36. The illumination 28 provides a circle or ellipse of light on the device that encompasses a portion of the image area 60.

As shown in FIGS. 5 and 6, each light source 40 in a particular row is positioned such that its central ray 32 is approximately directed to a single image point 36 and further such that each light source in that row is equidistant (approximately radius R) from image point 36. Image plane 22 is the horizontal plane of the PWB that is positioned such that the image point 36, image axis 48, and scan axis 18 are contained on the image plane 22. The image area 60 on the PWB encompasses the image depth 24 and the image width 44 on image plane 22. Each light source 40 has a light contribution 28 (represented by the hatched area for one light source 40 in FIG. 5) that extends beyond the image depth 24. While the central rays 32 from each light source 40 point to approximately the center of the image area 60, the overall illumination from each light source 40 overfills the image area 60. In other words, each light source has an illumination contribution 28 that covers more than the image depth 24. The most intense light from each light source 40 is at the image point 36 and the light intensity falls off progressively at distances further away from the image point 36 along the image plane 22. The intensity provided by the use of a multitude of light sources 40 results in a greater light intensity so that the central ray 32 of each light source 40 does not have to be precisely aligned to the image point 36. The overfill of these many light sources will average and results an illumination that approximates a uniform illumination from a single light source. Furthermore, the image width 44 can also be overfilled to provide uniform illumination throughout the entire image area 60. At a minimum, the width of the illumination from the light sources must meet the width of the field of view width of interest (as defined by the camera used). For imaging using a line scan camera, an overfill of approximately one inch on either side of the image depth 24 and either side of the image width 44 is more than adequate to provide the light uniformity necessary for automated inspections of PWBs.

FIG. 5 further illustrates that the dome light array 20 of the present invention provides illumination from a variety of angles. Light source 40' provides illumination from a very low incident angle 42, while light source 40" provides illumination from a very high incident angle 42. The remaining light sources 40 provide illumination from varying angles between the angle of light source 40' and the angle of light source 40". The low angle illumination allows for improved inspection of vertical leads in the scan axis 18. Narrow angle illumination causes glinting where the percentage of the light that is glinting is relatively high. The wide angle illumination provided by the present invention distributes the light that would potentially cause glinting over a wider to reduce the percentage of actual light that is glinting. While wide angle illumination still invites glinting from all of the angles, the energy from each of those glints is greatly reduced to lessen the occurrence of saturation in digital cameranglea cells.

Illumination system 10 can be extended along image axis 48 to accommodate different image widths 44. The radius R may be changed to allow for varying standoff from the imaging area. By increasing the radius R, the light sources 40 within illumination system 10 can be located further away from the image plane 22, and still maintain the low angle illumination properties. As the radius R increases, the area of the light array increases, allowing for more light sources 40 to be incorporated into the dome light array 20. Typically, the intensity of a given light source 40 falls off as the square of the distance. However, by using light sources 40 with integral lenses, and specific angles of illuminations, the working radius R can be extended over a large range. Because each light source 40 on the circumference is directed to the same point on the image area 60, and because light from adjacent light sources 40 overlaps along the axis, the intensity of light tends to average and become uniform.

Figure 8A:
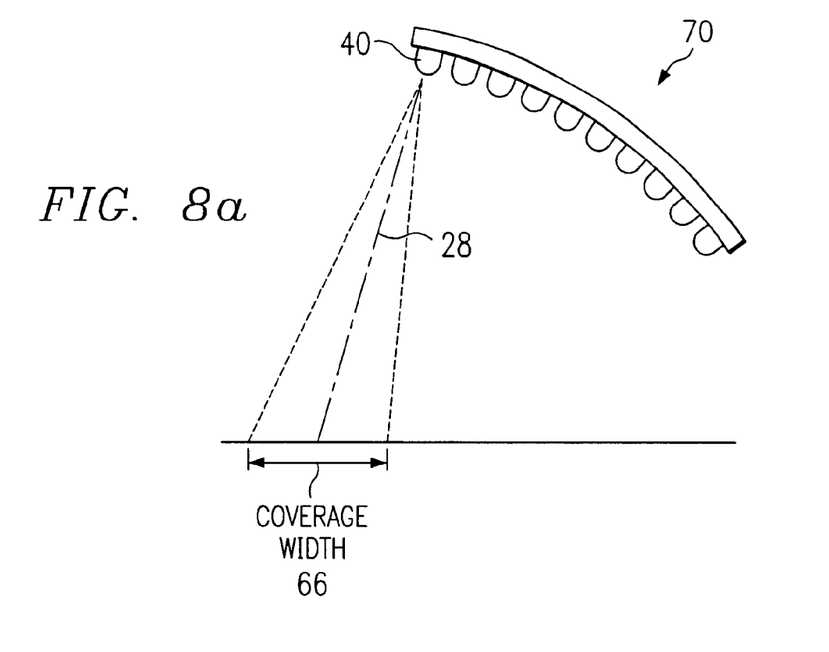
FIGS. 8A and 8B illustrate the difference in light source light source illumination with and without an optical lens to show the concentration of light using an optical lens.
Figure 8B:
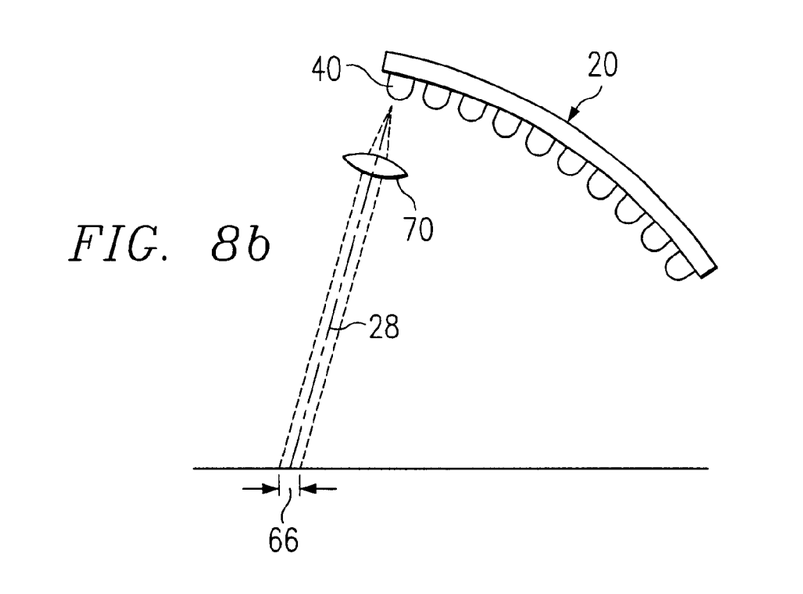

Improvement in uniformity and intensity of light in the image area 60 can be achieved by incorporating a short focal length cylindrical lens 70 in conjunction with each light source 40. The diverging beam can be collimated or focused over the depth of the image area 60, while the same smoothing caused by overlapping beams will still make the line of light intensity uniform and smooth. FIGS. 8A and 8B illustrate the differences in these types of light sources. In FIG. 8A, the light source 40 provides a diverging illumination area 28 that has a coverage width 66. By adding a cylindrical imaging optic 70 to a point source (e.g., a small filament or LED chip), the light is focused along one dimension and allowed to diverge along the other. When pointed at a flat surface normal to the light source 40 and lens 70, a line of light would be presented. By rotating the light source 40 and lens 70 about its cylindrical axis and adjusting the angular parameters, the line of light can be directed to coincide with the image area 60 with a coverage width 66 that is greatly contracted. This results in less wasted light. Adjusting the position of the line of light on the image area 60 can help create a more uniform illumination field along the length of the image area 60. Methods of generating the line of light can include separate cylindrical optics 70 on each light source 40, or alternatively, molding a cylindrical optic 70 into the light source itself (LEDs are a likely candidate) or creating an array of cylindrical lenses 70 in a mask that would be used to hold the light sources 40 at the correct angles and cast the line of light at the subject.

The requirements for a quality image exist along the image axis 48 as they do along the scan direction or scan axis 18 (i.e., lighting of adequate intensity and from as full a range of angles as possible). While the dome light array 20 provides excellent uniform lighting from a broad range of angles along the scan axis 18 of the imaged area, adequate illumination from the end of the image area 60 (along image axis 48) to eliminate shadowing may require additional illumination. The side panel light arrays 30 can provide this type of illumination for leads and other components along the image axis 48.

Three alternative embodiments of side panel light arrays 30 are provided for illumination along the image axis 48. As intensity requirements increase, due to the width of the image area 60 or sensitivity issues with the camera, the complexity of the illumination panel may be increased to improve efficiency. For each embodiment described and shown in FIGS. 4 and 7, the side panel light array 30 has a plurality of light sources 40 where the light sources 40 are aligned in approximately parallel rows 51. The illumination system 10 can include a side panel light array 30 attaches to both sides of the dome light array 20 to provide lighting along the image axis 48 from both sides toward the interior of the illumination system 10.

The light sources 40 can include LEDs, and particularly can include diffuse LEDs. Diffuse LEDs have a frosted appearance, essentially making the surface of the light source 40 a light emitter, making the light source 40 appear larger. The illumination cast by such a light source 40 is distributed over a large angle, so that even if the light source 40 is not directly pointed at the image area 60, some light from the light source 40 will fall on the region of interest. Other types of lighting elements can also be used for light sources 40.

Figure 4:
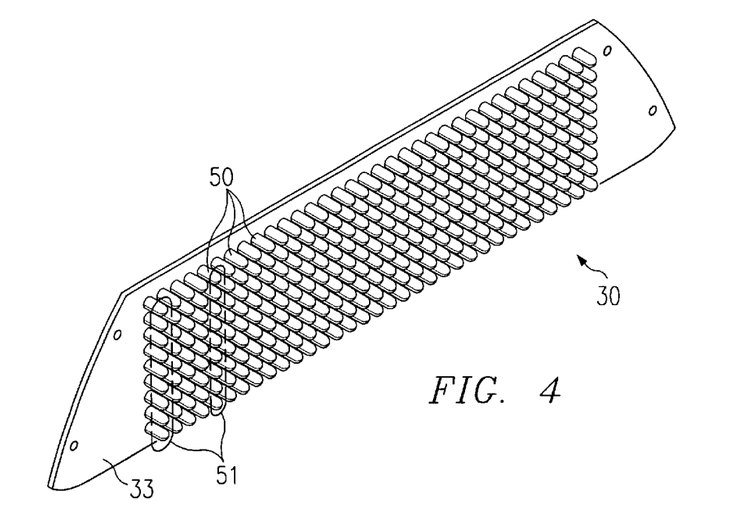
FIG. 4 is an embodiment of a side panel light array of the present invention including light sources that are LEDs.

For the embodiment of FIG. 4, the light sources 40 are positioned such that the central light ray from each LED 40 shines approximately perpendicular to the side panel frame 33 (i.e., at a ninety degree angle from side panel light array 30). Thus, if the side panel light array 30 is mounted at a right angle to the frame 14 on each side of dome light array 20 (as shown in FIGS. 1 and 2), then the light sources 40 from each side panel light array 30 are pointed at one another along the image axis 48. Using this embodiment of the side panel light array 30 with intense, diffuse light sources 40 will result in a very broad light source that floods the interior, and thus the image area 60, with light from an extended range of angles. By using a large number of diffuse light sources 40, enough intensity can be generated to provide adequate fill light along the image axis 48. Even if no light source 40 is directly pointed at the image area, some light from each light source 40 will fall on the region of interest. While most of the optical energy is not incident on the image area 60, the light that does fall on the image area 60 is reasonably uniform and even. The side panel light array 30 of FIG. 4 provides approximately uniform illumination over a vertical area from a two-dimensional horizontal surface. The side panel light array 30 embodiment of FIG. 4 could also be attached to the side of the dome light array 20 at an angle such that the light from the light sources 40 points downward toward the image plane 22.

Figure 7:
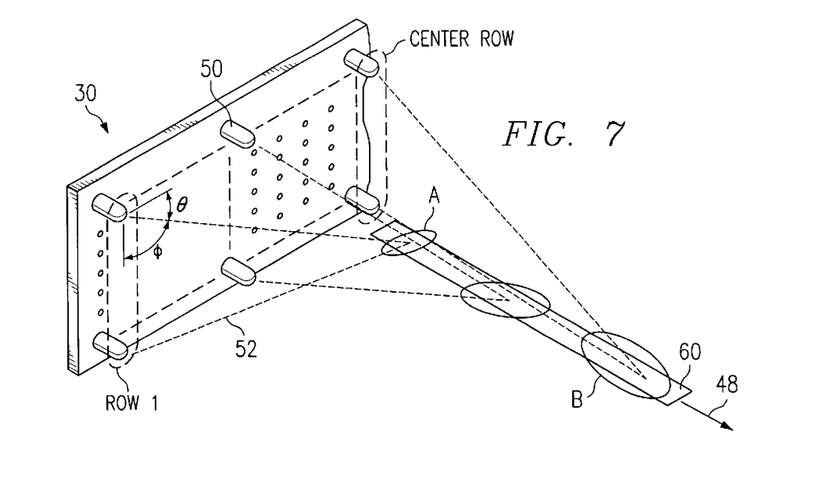
FIG. 7 illustrates another embodiment of the side panel light array having a different light source directional arrangement.

In cases where simple diffuse LED light sources do not provide adequate energy, a focused side panel light array 30 can be constructed to illuminate along the image axis 48. This type of side panel light array 30 can use LEDs 40 having clear lenses and where each vertical row of light sources 40 is rotated to throw light over an angle determined by the field of view to be covered and the number of light elements in the array. FIG. 7 shows a partial view of a side panel light array 30 with focused image axis illumination. As shown, each light source 40 within a vertical row of light sources 40 is rotated (as compared to the position in FIG. 4) and positioned so that the central optical ray 52 from each light source 40 in a particular vertical row is directed at a specific point within the image area 60. Thus, each section within the image area 60 on the PWB would be illuminated by a series of light sources 40, but from different angles. For example, the light sources 40 in the vertical row labeled row 1 would illuminate the section of the image area 60 labeled Area A. Though only the upper and lower light sources 40 are shown, it should be understood that other light sources 40 can be contained in row 1 between these two light sources. Each light source 40 in row 1 would be positioned within side panel light array 30 so that the central ray 52 would illuminate approximately the center of Area A within image area 60. As shown, this allows illumination of the portion of Area A on image area 60 from a variety of illumination angles. Thus, the more light sources 40 on the side panel light array 30, the greater number of illumination angles. As shown in FIG. 7, each row of light sources 40 can be positioned to equalize, as much as possible, the distance the light from each light source 40 must travel to each point along the image area 60 width. Equalizing the distance the light from each light source 40 travels provides more uniform lighting.

For example, as shown, Row 1 of light sources 40 illuminate the portion of the image area 60 that is closest to side panel light array (i.e., area A), while the row of light sources 40 labeled "Center Row" are set to cast their light at the far end of the image area (labeled Area B). As the distance from the end of the imaging area 60 to the light sources 40 increases, the light sources 40 would cast their illumination progressively closer to the end of the image area 60 nearest the side panel light array 30. By doing this, the present invention reduces lighting unevenness caused by the expanding properties of light caused by the fact that the intensity of light falls off as function (typically square) of the distance from the light to the subject. By positioning the light sources with appropriate angles of illumination, less light will fall on non-image areas, increasing the intensity on the image area 60. This could be accomplished with a side panel light array 30 having fixed light sources located in holes that would have a unique pointing direction definable by two angles—the downward angle φ which defines how far from perpendicular toward the image plane the central ray will point and the inward angle θ which defines how far from perpendicular toward the center of the side panel light array 30 the central ray 52 will point.

Yet another embodiment of the side panel light array 30 would incorporate the focused array concept with the light source 40 as described in FIG. 7, but would additionally include the cylindrical imaging optics 70 of FIG. 8B on each light source element 40. This provides the advantages of both a focused direction and a reduced illumination width. Thus, instead of focusing a row of light sources 40 at the same image point 36, each light source 40 can be pointed at a different image point 36 to form a line of light across the image depth 24. By aiming each adjacent light source 40 in a vertical row to an adjacent image point on the image area, the entire image area 60 can be covered by a single row of light sources 40. By having each row of light sources 40 covering the entire image area 60, the image area is illuminated from the side panel light array 30 from a multitude of angles.

Liquid cooling of the light sources 40 and light sources 40 can be used to help maintain long working life at elevated light output levels. Alternatively, a fan could be incorporated within the dome light array 20 to force air from the area above the image plane out through a vent. The fan and vent could also address the problem of heat shimmering that can cause optical distortion. A PWB can be hot when it enters the automated inspection system. Hot air has a different density and different optical property than room temperature air and can cause optical distortion. Using a fan in conjunction vents cut into the cover 16 of the dome light array 20 can allow the hot air to be vented away from the optical path of the line scan camera. For some cameras, peak light intensity can be increased up to 10 times using duty cycle constrained impulse drivers.

Figure 9A:
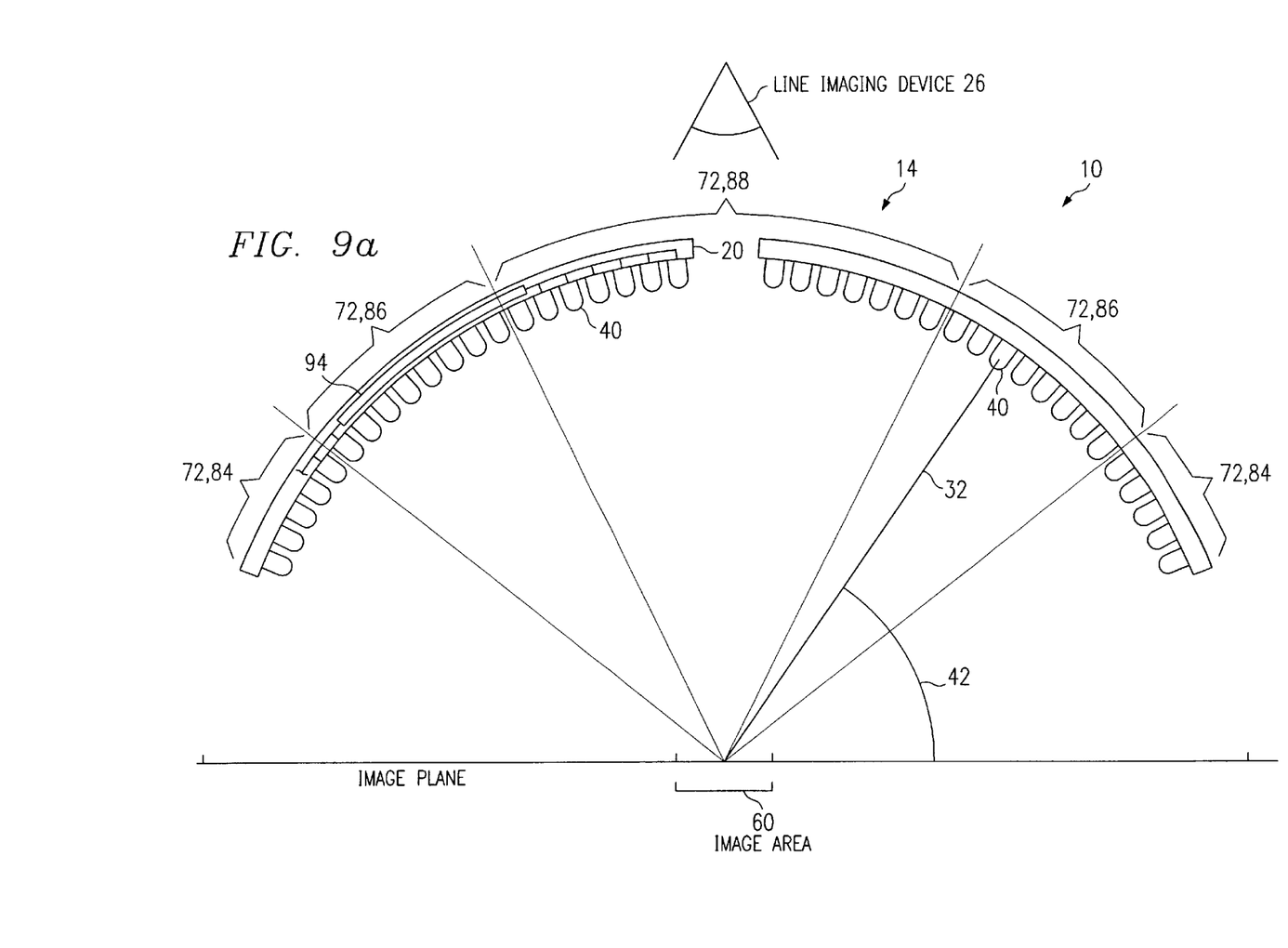
FIGS. 9A–9C illustrate an embodiment of the illumination system having the light sources arranged in light source groups which are each configured to produce a different wavelength of light.

The illumination system 10 can include a plurality of light source groups 72 as illustrated in FIG. 9A. The light sources 40 within each light source group 72 are configured to produce the same or approximately the same wavelength of light. Additionally, the wavelength of light produced by the light sources 40 within each light source group 72 can be different from the wavelength of light produced by the light sources 40 in the remaining light source groups 72. FIG. 9A illustrates the light sources 40 arranged in clusters in that at least a portion of the light sources from a single light source group are positioned adjacent to one another. Further, the light sources from a single light source group can be arranged in more than one cluster. For instance, FIG. 9A illustrates the light sources of a first light source group 84 arranged in two clusters. In other embodiments, the light sources 40 belonging to a single light source group 72 are not arranged in clusters but are dispersed throughout the frame 14. For instance, all the light sources which are closest to a single light source can belong to another other light source groups.

When the illumination system 10 includes light source groups 72, one or more imaging devices can be used to concurrently generate multiple images of the device. For instance, imaging devices such as line scan cameras often include a channel configured to generate an image using red light, a channel configured to generate an image using green light and another channel configured to generate an image using blue light. The illumination system 10 can include a first light source group 84 configured to produce red light, a second light source group 86 configured to produce green light and a third light source group 88 configured to produce blue light. Hence, a channel of the line scan camera can generate a first image from the light produced by the first light source group 84, another channel can generate a second image from the light produced by the second light source group 86 and another channel can generate a third image from the light produced by the third light source group 88. Images generated using different wavelengths of light can reveal different features of a device. Since, each image can be independently inspected for the features which the image best reveals, the invention improves the quality of the inspection process.

In one embodiment of the invention, each light source group 72 is associated with one or more ranges of incident angles 42. For instance, each light source group 72 can include the light sources 40 producing a central ray 32 which is incident on the image area 60 within a particular range of incident angles 42. The incident angle 42 is the angle between the central ray 32 and the image area 60. FIG. 9A illustrates an embodiment of the frame 14 including three light source groups 72. More than one light source group 72 can be associated with the same range of incident angles 42. Alternatively, two light source groups 72 can be associated with overlapping ranges of incident angles 42. However, each light source group 72 can be associated with a different range of incident angles 42 as illustrated in FIG. 9A. For instance, the first light source group 84 can include light sources 40 producing a light beam having a central ray 32 with an angle of incidence of less than about 35 degrees. The second light source group 86 can include light sources 40 which produce a light beam with a central ray 32 with an angle of incidence from about 35 degrees to about 65 degrees. The third light source group 88 can include light sources 40 which produce a light beam having a central ray 32 with an angle of incidence greater than about 65 degrees.

When the light source groups 72 are each associated with one or more ranges of incident angles 42, each of the images generated using the light from a particular light source group 72 is also associated with a particular range of incident angles 42. For instance, a first image generated from the light produced by the first light source group 84 would provide an image of the device as if the device were illuminated from less than 35 degrees. Additionally, a second image generated from the light produced by the second light source group 86 would provide an image of the device as if the device were illuminated from about 35 degrees to about 65 degrees. Further, a third image generated from the light produced by the second light source group 86 would provide an image of the device as if the device were illuminated from greater than about 65 degrees. Accordingly, the first image is associated with incident angles 42 less than about 35 degrees, the second image is associated with incident angles 42 from about 35 degrees to 65 degrees and the third image is associated with incident angles 42 greater than about 65 degrees.

Having images of a device which are associated with different incident angles 42 can enhance the inspection process. For instance, low incident angle 42 illumination may enhance edges to a greater extent than high incident angle 42 illumination, however, higher incident angle 42 illumination is more useful for inspection of plated through holes than is lower incident angle 42 illumination. As a result, the image associated with low incident angle 42 illumination is consulted for edge inspection while the image associated with higher angle illumination is consulted for plated through hole inspection.

Figure 9B:
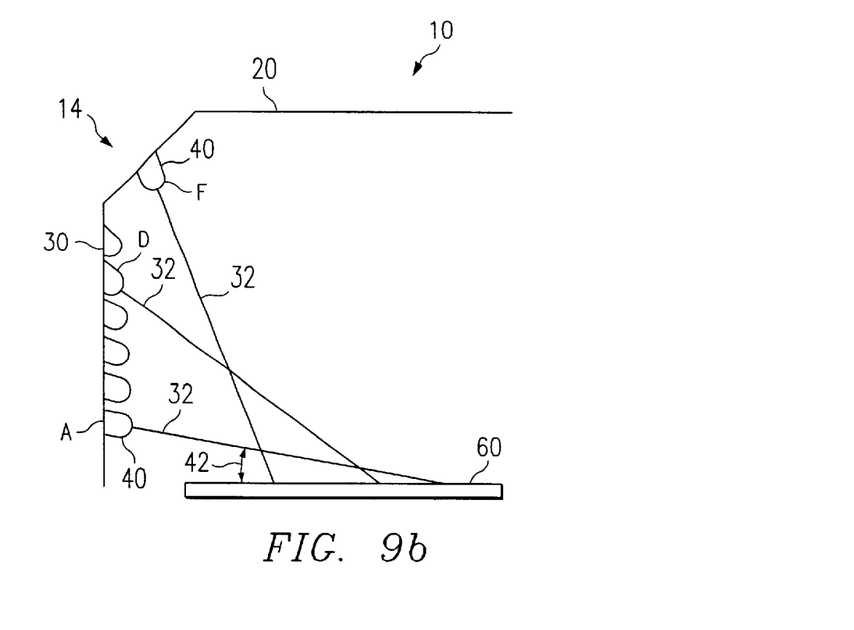
Figure 9C:
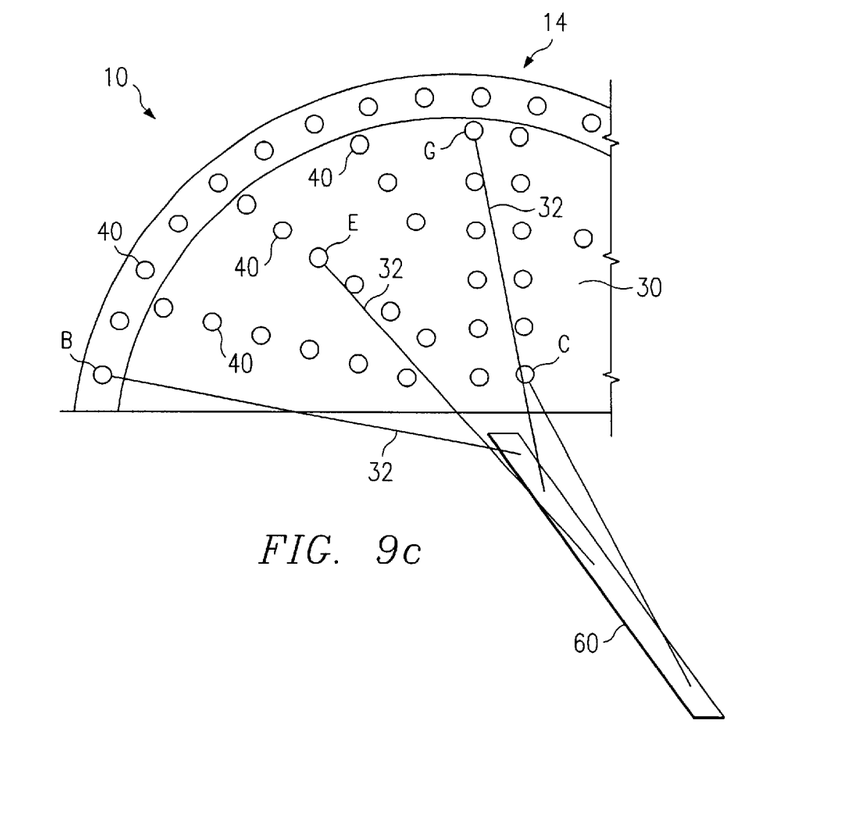

FIGS. 9B and 9C illustrate a side panel of the frame 14 illustrated in FIG. 9A. The light sources 40 included in the side panel are also be included in the light source groups 72. FIG. 9B is a sideview of the side panel looking along the scan axis 18. FIG. 9C is a sideview of the side panel looking perpendicular to the scan axis 18. The light sources 40 on the side panel are angled such that a central ray 32 of each light source 40 is incident on the image area 60. The light sources 40 can be angled in any pattern or they can be angled to equalize, as much as possible, the distance the light from each light source 40 to the image area 60 as discussed with respect to FIG. 7. As illustrated in FIG. 9B, the angle of the light source 40 in the side panel determines the angle of incidence between the central beam and the image area 60.

The light sources 40 in the side panel are assigned to the first light source group 84, the second light source group 86 and the third light source group 88 using the same incident angle 42 limitations used to assign the light sources 40 of FIG. 9A. For instance, the light sources 40 having a central ray 32 which is incident upon the image area 60 at an angle of incidence of less than about 35 degrees is included in the first light source group 84 discussed with respect to FIG. 9A. Accordingly, the light sources 40 labeled A, B and C are all assigned to the first light source group 84. Additionally, the light sources 40 having a central ray 32 with an angle of incidence from about 35 degrees to about 65 degrees is included in the second light source group 86. Accordingly, the light sources 40 labeled D and E would be assigned to the second light source group 86. Further, the light sources 40 having a central ray 32 with an angle of incidence greater than about 65 degrees are included in the third light source group 88. Accordingly, the light sources 40 labeled F and G would be assigned to the third light source group 88.

Although three light source groups 72 are illustrated in the illumination systems 10 of FIGS. 9A–9C, an illumination system 10 according to the present invention can include more than three light source groups 72 and as few as two light source groups 72. Additionally, the light source groups 72 are not limited to the ranges of incident angles 42 disclosed above. For instance, a light source group 72 can include the light sources 40 producing central rays 32 which are incident upon the image area 60 at less than 45 degrees and in some instances less than 35 degrees. Additionally, a light source group 72 can also include the light sources 40 producing a central ray 32 which is incident on the image area 60 between 25 and 75 degrees and in some instances between 35 and 65 degrees. Further, a light source group 72 can include the light sources 40 producing a central ray 32 which is incident on the image area 60 at greater than 55 degrees and in some instances greater than 65 degrees.

Suitable light sources 40 for use in the light source groups 72 include, but are not limited to light emitting diodes (LEDs). LEDs are available which produce a particular wavelength of light. Each light source group 72 can include LEDs which produce a particular wavelength of light. For instance, a first light source group 84 can include red LEDs, a second light source group 86 can include green LEDs and a third light source group 88 can include blue LEDs. In this embodiment the light source groups 72 are fixed in that a light source group 72 can only be changed by physically removing the light sources 40 from the frame 14.

In an alternative embodiment of the illumination system 10, the light source groups 72 can be varied. The frame 14 can include LEDs which can be controlled to produce more than one wavelength of light. For instance, LEDs are available which can be controlled to produce red light, green light, blue light and combinations of these colors. These LEDs can be used for every light source 40 in the illumination system 10. Hence, each light source 40 is physically the same in this embodiment.

The illumination system 10 can include electronics 74 in communication with the light sources 40 for controlling the wavelength of light produced by each such LEDs as illustrated in FIG. 9A. The electronics 74 can be coupled with the frame 14 or can be movable with respect to the frame 14. The electronics 74 can be used to change the wavelength of light produced by a light source group 72. Further, the light sources 40 included in each light source group 72 can be changed. For instance, a light source group 72 including light sources 40 associated with an angle of incidence less than 35 degrees can be changed to include light sources 40 associated with an angle of incidence less than 45 degrees. This change can be achieved by changing the wavelength of light produced by the light sources 40 associated with angles of incidence between 35 degrees and 45 degrees such that these light sources 40 are configured to produce the same wavelength of light as the light sources 40 associated with angles of incidence less that 35 degrees.

Suitable electronics 74 for controlling the light sources 40 can include one or more processors. Suitable processors include, but are not limited to, microprocessors, a digital signal processors (DSP), integrated circuits, application specific integrated circuits (ASICs), logic gate arrays and switching arrays. The electronics 74 can also include one or more memories for storing instructions to be carried out by the one or more processors and/or for storing data developed during operation of the illumination system 10. Suitable memories include, but are not limited to, RAM and electronic read-only memories (e.g., ROM, EPROM, or EEPROM).

Suitable imaging devices for use with an illumination system 10 including light source groups 72 include color cameras and line scan cameras such as a Dalsa CLT5. As described above, many line scan cameras include channels which are sensitive to different wavelengths of light. Line scan cameras are able to concurrently generate the image for each channel. As a result, using a line scan camera as the imaging device can increase the efficiency of image generation. Additionally, the information obtained in a channel can be combined with the information in other channels in order to generate composite image.

Another embodiment of the imaging device includes a plurality of gray scale cameras focused on the image area 60. A dichroic filter can be positioned in front of each gray scale camera. The filters can be configured such that each gray scale camera primarily receives a wavelength of light produced by a single light source group 72. Accordingly, each gray scale camera generates an image from the light produced one light source group 72. Further, there is preferably one gray scale camera configured to receive the light from each light source group 72. Each gray scale camera can concurrently generate an image of the device in order to increase the efficiency of the device inspection process. Other imaging devices which are not described here are also suitable for use with an illumination system 10 according to the present invention.

Imaging devices are often more sensitive to certain wavelengths than they are to other wavelengths. For instance, cameras are often more sensitive to shorter wavelengths of light than longer wavelengths. Additionally, light sources 40 producing light beams which strike the image area 60 at a low angle of incidence reflect less light toward the imaging device than do light sources 40 producing light beams which strike the image area 60 at higher angles of incidence. The sensitivity of the image device and the reflection characteristics can be taken into consideration when positioning the light sources 40 within the frame 14. For instance, the light source groups 72 associated with low angles of incidence can be chosen to produce shorter wavelength light than the light source groups 72 associated with higher angles of incidence. In this arrangement, the increased sensitivity of the imaging device to the low wavelength light can compensate for the reduced ratio of low wavelength light reflected toward the imaging device.

FIGS. 9A to 9C provide an illustration of the above rule for placement of light source groups 72 within a frame 14. Hence, given three light source groups 72 configured to produce red light, green light and blue light arranged in light source groups 72 illustrated in FIG. 9A, the first light source group 84 can include the red light sources 40, the second light source group 86 can include the green light sources 40 and the third light source group 88 can include the blue light sources 40. This arrangement will at least partially compensate for the reduced degree of reflection toward the imaging device given the added sensitivity of the imaging device to the red light. Additionally, the reduced sensitivity of the imaging device toward the blue light is compensated for by increased ratio of light reflected to the imaging device which results from the high angle of incidence.

Although the present invention has been described in detail, it should be understood that various changes, combinations, substitutions and alterations can be made hereto without departing from the spirit and scope of the invention as described by the appended claims.

What is claimed is:

1. An illumination system for inspection of devices, comprising:
    a partially cylindrical dome frame for positioning over an image area; and
    a plurality of light source groups coupled with the frame, each light source group configured to produce a wavelength of light which is not produced by another light source group, wherein each light source group has a distinct range of incident angles.

2. The system of claim 1, wherein the light source groups include light sources arranged in a cluster.

3. The system of claim 1, wherein each light source group includes a plurality of light sources and each light source group includes all the light sources producing a central ray which is incident on the image area within one or more distinct ranges of incident angles.

4. The system of claim 1, wherein one of the light source groups includes light sources producing a central ray which is incident upon the image area at less than 45 degrees.

5. The system of claim 1, wherein one of the light source groups includes light sources producing a central ray which is incident on the image area between 25 and 75 degrees.

6. The system of claim 1, wherein one of the light source groups includes light sources producing a central ray which is incident on the image area at greater than 55 degrees.

7. The system of claim 1, wherein the light source groups include light emitting diodes.

8. The system of claim 1, wherein each light source group includes light sources which are each able to produce a single wavelength of light.

9. The system of claim 1, wherein each light source group includes light sources which are each able to produce more than one wavelength of light.

10. The system of claim 9, further comprising electronics for controlling the wavelength of light produced by a light source group.

11. The system of claim 9, further comprising electronics for selecting the light sources which are to be included in a light source group.

12. The system of claim 1, further comprising an imaging device configured to generate a plurality of images, each image being generated from a different wavelength of light.

13. The system of claim 12, wherein the imaging device is a line scan camera.

14. The system of claim 1, further comprising a plurality of gray scale cameras and one or more filters positioned between each camera and the image area.

15. A method for inspecting a device, comprising:
    positioning a partially cylindrical dome frame over an image area, the frame including a plurality of light source groups, each light source group is configured to produce a wavelength of light which is not produced by another light source group, wherein each light source group has a distinct range of incident angles; and
    generating a plurality of images, each image generated from the light produced by a different light source group.

16. The method of claim 15, wherein the light source groups include light sources arranged in a cluster.

17. The method of claim 15, wherein each light source group includes a plurality of light sources and each light source group includes all the light sources producing a central ray which is incident on the image area within one or more distinct ranges of incident angles.

18. The method of claim 15, wherein one of the light source groups includes light sources producing a central ray which is incident upon the image area at less than 45 degrees.

19. The method of claim 15, wherein one of the light source groups includes light sources producing a central ray which is incident on the image area between 25 and 75 degrees.

20. The method of claim 15, wherein one of the light source groups includes light sources producing a central ray which is incident on the image area at greater than 55 degrees.

21. The method of claim 15, wherein the light source groups include light emitting diodes.

22. The method of claim 15, wherein each light source group includes light sources which are each able to produce a single wavelength of light.

23. The method of claim 15, wherein each light source group includes light sources which are each able to produce more than one wavelength of light.

24. The method of claim 23, wherein each light source group is connected to electronics for controlling the wavelength of light produced by a light source group.

25. The method of claim 23, wherein each light source group includes electronics for selecting the light sources which are to be included in a light source group.

26. The method of claim 15, wherein generating an image includes providing an imaging device configured to generate the plurality of images.

27. The method of claim 26, wherein the imaging device is a line scan camera.

28. The method of claim 15, wherein generating an image includes providing a plurality of gray scale cameras and one or more filters positioned between each camera and the image area.

29. A method of illuminating a device to be inspected, comprising:
    positioning a partially cylindrical dome frame over an image area; and
    illuminating the image area from a plurality of light source groups attached to the frame, each light source group being configured to produce a wavelength of light which is not produced by another light source group, and wherein each light source group has a distinct range of incident angles.

30. The method of claim 29, wherein the light source groups include light sources arranged in a cluster.

31. The method of claim 29, wherein each light source group includes a plurality of light sources and each light source group includes all the light sources producing a central ray which is incident on the image area within one or more distinct ranges of incident angles.

32. The method of claim 29, wherein one of the light source groups includes light sources producing a central ray which is incident upon the image area at less than 45 degrees.

33. The method of claim 29, wherein one of the light source groups includes light sources producing a central ray which is incident on the image area between 25 and 75 degrees.

34. The method of claim 29, wherein one of the light source groups includes light sources producing a central ray which is incident on the image area at greater than 55 degrees.

35. The method of claim 29, wherein the light source groups include light emitting diodes.

36. The method of claim 29, wherein each light source group includes light sources which are each able to produce a single wavelength of light.

37. The method of claim 29, wherein each light source group includes light sources which are each able to produce more than one wavelength of light.

38. The method of claim 37, wherein each light source group is connected to electronics for controlling the wavelength of light produced by a light source group.

39. The method of claim 37, wherein each light source group includes electronics for selecting the light sources which are to be included in a light source group.

40. An illumination system for the inspection of devices comprising:
   a partially cylindrical dome frame for positioning over an image area;
   a first light source group comprising light sources operable to produce a first wavelength of light; and
   a second light source group comprising light sources operable to produce a second wavelength of light; and
   wherein each light source group has a distinct range of illumination angles.

41. The system of claim 40, further comprising a third light source group comprising light sources operable to produce a third wavelength of light, wherein each light source group has a distinct range of illumination angles.

42. The system of claim 41, wherein:
   the first light source group includes light sources producing a central ray which is incident upon the image area at less than 35 degrees;
   the second light source includes light sources producing a central ray which is incident on the image area from about 35 degrees to about 65 degrees; and
   the third light source group includes light sources producing a central ray which is incident upon the image area at greater than 65 degrees.

43. An illumination system for inspection of devices, comprising:
   a partially cylindrical dome frame, having a geometry defined by a radius beginning at an image axis on an image plane so as to form a partial cylinder about the image axis, for positioning over an image area; and
   a plurality of light source groups coupled with the frame and configured to produce one or more wavelengths of light, each light source group configured to produce a wavelength of light which is not produced by another light source group.

44. The system of claim 43, wherein the light source groups include light sources arranged in a cluster.

45. The system of claim 43, wherein each light source group includes a plurality of light sources and each light source group includes all the light sources producing a central ray which is incident on the image area within one or more ranges of incident angles.

46. The system of claim 43, wherein one of the light source groups includes light sources producing a central ray which is incident upon the image area at less than 45 degrees.

47. The system of claim 43, wherein one of the light source groups includes light sources producing a central ray which is incident on the image area between 25 and 75 degrees.

48. The system of claim 43, wherein one of the light source groups includes light sources producing a central ray which is incident on the image area at greater than 55 degrees.

49. The system of claim 43, wherein the light source groups include light emitting diodes.

50. The system of claim 43, wherein each light source group includes light sources which are each able to produce a single wavelength of light.

51. The system of claim 43, wherein each light source group includes light sources which are each able to produce more than one wavelength of light.

* * * * *